United States Patent [19]
Gregory et al.

[11] Patent Number: 5,170,823
[45] Date of Patent: Dec. 15, 1992

[54] DEVICE FOR FILLING AN ANAESTHETIC VAPORIZER

[75] Inventors: Raymond S. Gregory, Bingley; William W. Maude, Skipton, both of England

[73] Assignee: The BOC Group plc, Surrey, England

[21] Appl. No.: 669,141

[22] Filed: Mar. 14, 1991

[51] Int. Cl.⁵ .............................................. F16L 15/00
[52] U.S. Cl. .................................... 141/382; 141/384; 141/387; 285/914
[58] Field of Search ............... 141/382, 383, 384, 385, 141/386, 387, 98; 285/914, 24, 27, 12

[56] References Cited
U.S. PATENT DOCUMENTS
3,565,133  2/1971  Jones ................................... 141/308
4,665,960  5/1987  Bizezicki et al. ..................... 141/384
4,928,859  5/1990  Krohn et al. ......................... 141/382

FOREIGN PATENT DOCUMENTS
771968   4/1957  United Kingdom ............... 285/914
1394216  5/1975  United Kingdom .
2189472  10/1987 United Kingdom .
2177008  1/1989  United Kingdom .

Primary Examiner—Ernest G. Cusick
Attorney, Agent, or Firm—Roger M. Rathbun; Larry R. Cassett

[57] ABSTRACT

A combination of bottle, collar and cap where the bottle collar has a keying lug that interfits with a cap slot and which keying is necessary to screw the cap onto the bottle.

6 Claims, 4 Drawing Sheets

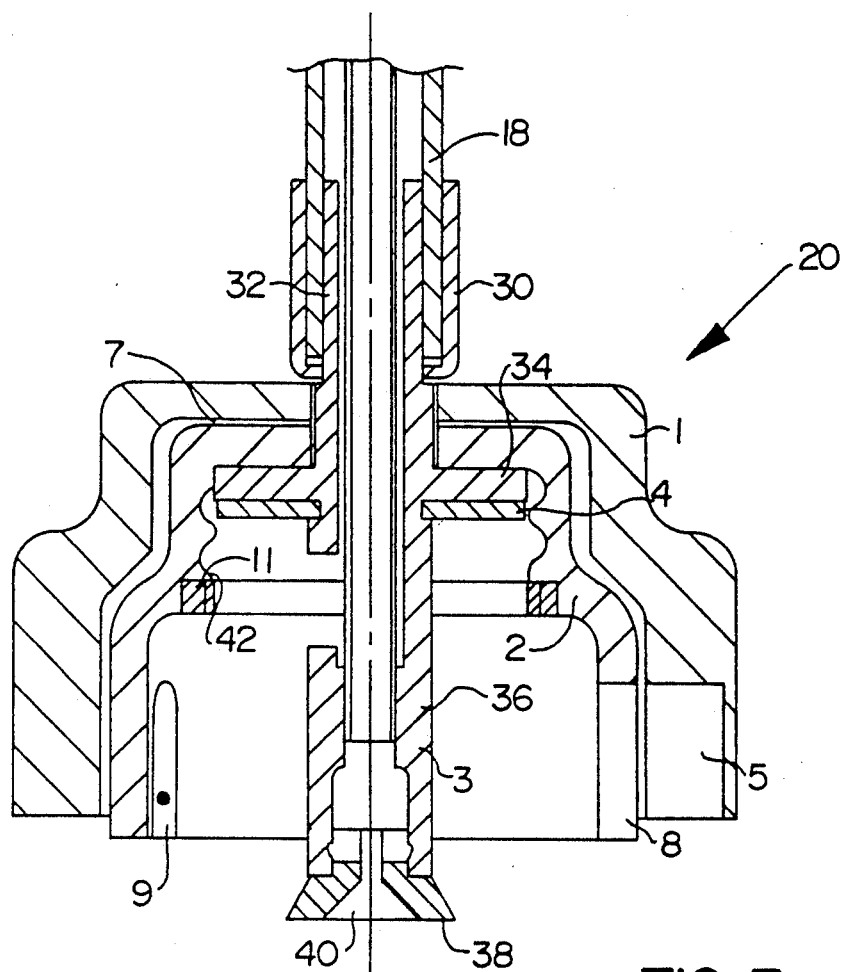
FIG. 3
FIG. 4
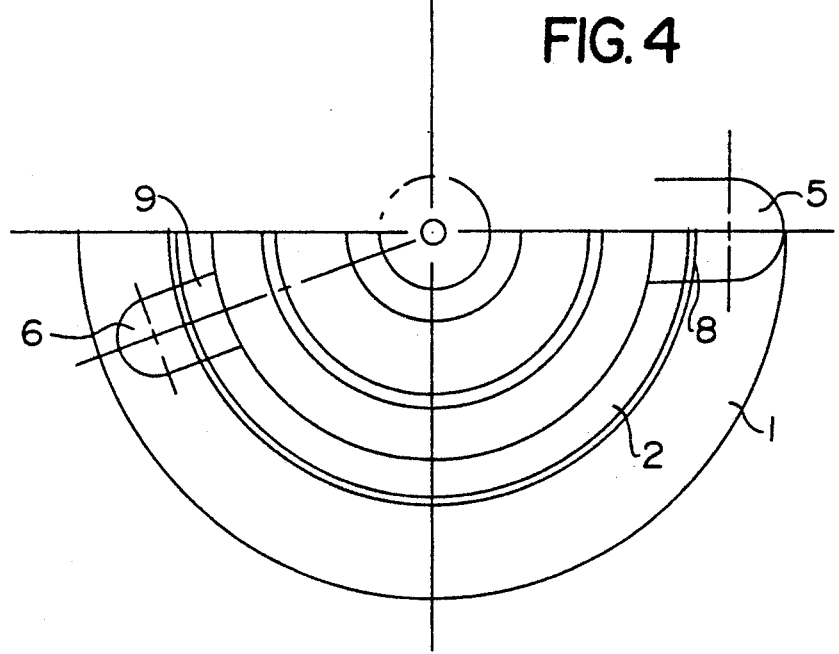

DEVICE FOR FILLING AN ANAESTHETIC VAPORIZER

BACKGROUND OF THE INVENTION

The present invention relates to anaesthetic vaporisers and in particular to devices for filling such anaesthetic vaporisers.

Throughout this specification the term "anaesthetic" is intended to embrace anaesthetic and analgesic agents.

As explained in UK Patent No. 1193241, anaesthetic vaporisers are used with anaesthesia machines for mixing the vapour of a volatile liquid anaesthetic with a carrier gas such as air, oxygen, nitrous oxide or a combination thereof.

Usually, an anaesthetic vaporiser is dedicated for use with only one type of anaesthetic and UK Patent No. 1193241 and UK Published Patent application Ser. No. 2189472 each describe a filling system which substantially eliminates the possibility of an anaesthetic vaporiser being filled with the wrong anaesthetic agent.

In these known systems, coding for drug type is achieved by the use of slots in a bottle adaptor which correspond to or co-operate with lugs formed on a free spinning keyed bottle collar placed on the neck of a bottle containing an anaesthetic agent. A bottle adaptor for one agent cannot be fastened to a bottle with a collar coded for a different agent.

Criticism of this known system has been made on the grounds that bottles containing anaesthetic agents may not always have a coded collar fitted and that the same bottle neck thread is used for a large number of different anaesthetics, as well as for liquids other than anaesthetic liquids. Consequently, in the absence of a collar from the neck of a bottle, there is a significant risk of an incorrect bottle adapter being fastened to a bottle.

SUMMARY OF THE INVENTION

It is an aim of the present invention to prevent or inhibit the attachment of a bottle adaptor to a bottle which does not have an appropriate coded collar in place on the bottle.

According to the present invention, there is provided a combination of a bottle, collar and a cap connector for connecting the bottle to fluid delivery means. The collar and the bottle are conventional and include the same freely rotatable collar on bottles as used with prior art filling systems where such collar surrounds the neck of the bottle and formed with at least one axially extending lug, the cap connector including a cap, the cap and the bottle having mating circumferentially extending screw threads, the cap including at least one axially extending slot for receiving the lug of the collar, and an outer sleeve freely rotatable around and substantially covering the cap, said outer sleeve having at least one axially extending slot in register with the slot in the cap for receiving the said lug, the arrangement being such that mating of the lug in the slot of the cap and the outer sleeve respectively is necessary before relative rotation between the outer sleeve and the cap on the one hand, and the bottle on the other hand, is possible to screw the cap into engagement with the bottle.

The connection technique of the present invention has the advantage that it is not, in fact, possible to rotate the cap relative to the bottle, to screw the cap into engagement with the bottle, unless the bottle is fitted with a coded collar having lugs by which relative rotation between the outer sleeve and the cap can be prevented. It is therefore only possible to dispense a fluid from a bottle when the bottle is fitted with an appropriately coded collar, reducing the possibility of a drug being dispensed incorrectly from a bottle.

Preferably, the cap connector includes a central main core, about which the cap and the outer sleeve are independently freely rotatable. An appropriate seal is provided between the cap and the central main core so that leakage of fluid from the cap is reduced to an acceptable low level.

Preferably, the cap connector is arranged so that the level of friction between the outer sleeve and the cap is less than the level of friction between the cap and the bottle to which the cap connector is to be fitted. For example, a washer might be included between a surface of the cap and an adjacent surface of the outer sleeve, formed from a low friction material; a suitable material is polytetrafluoroethylene. Alternatively, or in addition, a quantity of a high friction material may be provided between a surface of the cap and an adjacent surface of the bottle. A suitable material might be, for example, an elastomer.

Preferably, the open end of the cap extends axially beyond the open end of the outer sleeve, in a direction towards the bottle. This has the advantage that a user can engage the slots in the cap with the lugs on the collar before rotating the sleeve relative to the cap then to align the slots in the sleeve with the lugs.

Coding of the collar on the bottle and of the slots on the cap and the outer sleeve can be achieved for example by the position of the formations around the periphery of the respective components, or by the radial extent of the formations, or both. For example, the lugs on the collar may have a relatively small radial extent, and the slots in the outer sleeve may be blind spots. Alternatively or in addition, lugs may be provided which have a greater radial extent, and the slot sin the outer sleeve may extend through the entire thickness of the sleeve.

It can be preferred that the wall thickness of the cap vary around its circumference. For example, in a preferred construction, the wall thickness varies between minimum and maximum values at respective points which are diametrically opposite to one another. Generally, the internal and external walls of the cap will be essentially circular, so that the circular neck of the bottle can be received within the cap, and so that a circular outer sleeve can fit over the cap. The variation in wall thickness of the cap will generally result in the outer sleeve being mounted eccentrically relative to the axis of the bottle and of the internal cross-section of the cap. An advantage of a construction in which the wall thickness of the fitting of the lugs on the collar into the respective slots in the cap is facilitated, even when the radial extent of respective ones of the lugs varies. For example, an advantage of a constructions in which the wall thickness of the cap varies around its circumferent is that, having first engaged the lugs of the collar into the respective slots in the cap, it can be so arranged that only one lug projects beyond the cap and that when the outer sleeve is rotated the slot or recess provided in the sleeve engages easily with the lug. If the cap had a constant wall thickness and the collar had more than one projecting lug then the outer sleeve might have to engage with more than one lug in order to lock the sleeve and cap together and enable the cap to be screwed into place. Since the lugs may be of different sizes and of non-symmetrical orientation then it might be possible to engage a sleeve recess or slot with one of the lugs, whilst the remaining lug(s) and recess(es) or slot(s) were not correctly aligned. This could result in distortion or other difficulties arising when attempting to screw the cap onto the bottle.

BRIEF DESCRIPTION OF THE DRAWINGS

An embodiment of the invention will now be described by way of example reference being made to the Figures of the accompanying diagrammatic drawings in which:

FIG. 3 is a sectional view of a cap connection forming part of a bottle adaptor modified to prevent or inhibit the attachment of the bottle adaptor to a bottle which does not have an appropriate coded collar in place on the bottle;

FIG. 4 is a partial plan of the cap connection of FIG. 3; and

DETAILED DESCRIPTION OF THE PREFERRED EMBODIMENT

Figure 1:
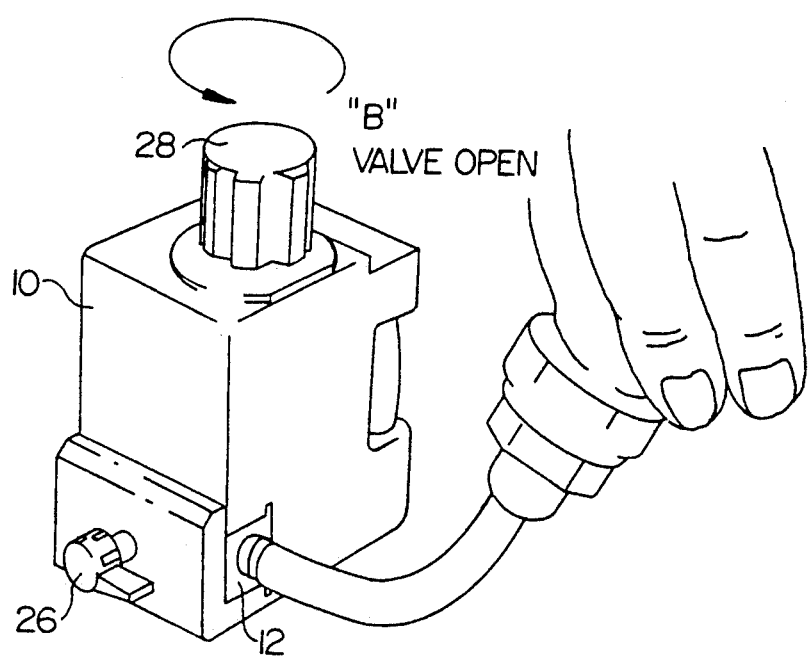
FIG. 1 is a perspective view of a known filler block forming part of an anaesthetic vaporiser which is being filled with a liquid anaesthetic agent.
Figure 2A:
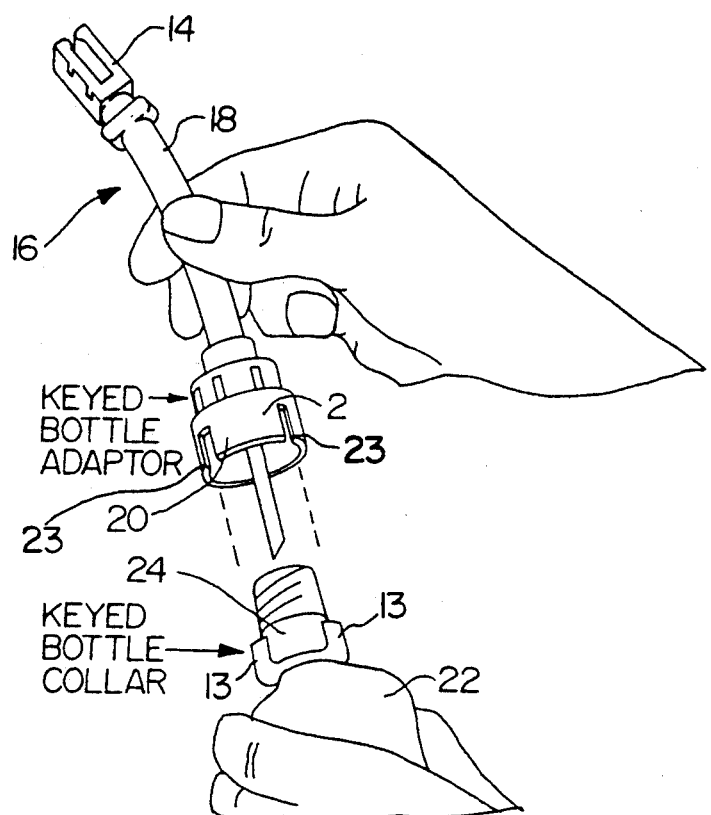
FIG. 2 is a perspective view showing a known keyed bottled adaptor about to be connected to a bottle containing a liquid anaesthetic agent onto which bottle a coded collar is mounted.
FIG 2B is a perspective view showing a known keyed bottle adapter connected to a bottle.
Figure 2B:
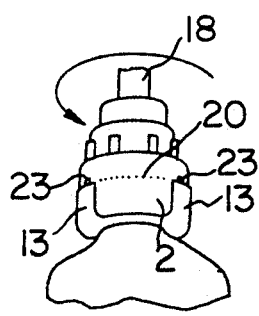

Referring first to FIGS. 1 and 2, a filler block 10 forming part of an anaesthetic vaporiser (not shown) includes an opening 12 which receives an outlet termination 14 forming part of a bottle adaptor 16. The bottle adaptor 16 includes a tube 18 connecting the outlet termination 14 to a cap connector 20. The cap connector 20 is screwed on to the threaded neck of a bottle 22 containing anaesthetic agent and slots in a cap 2 forming part of the cap connector 20 co-operate with lugs 13 on a coded collar 24 arranged around the neck of the bottle 22. Said bottle adaptor 16 is connected to the bottle 22 ready for filling the anaesthetic vaporiser with liquid anaesthetic agent.

Usually the outlet termination 14 is keyed, for example, a slot is positioned and/or dimensioned to mate with a locating tongue or peg on the filler block 10 so that only an outlet termination 14 of the correct shape can enter the opening 12.

When the outlet termination 14 is located in the opening 12 a clamp lever 26 is tightened and the bottle 22 is lifted as illustrated in FIG. 1. Next the valve 28 is opened allowing liquid anaesthetic agent to enter the vaporiser via the filler block 10 from the bottle 22.

The above described bottle adaptor and method of filling an anaesthetic vaporiser are well known.

Referring now to FIGS. 3 and 4 where like reference numerals denote like features there is shown a cap connector 20 forming part of a bottle adaptor 16.

The bottle adaptor 16 includes a tube 18 connecting the cap connector 20 to an outlet termination (not shown in FIGS. 3 and 4). The tube 18 is secured by means of a ferrule 30 to a tail-piece 32 of a main core 3. The main core 3 further includes a laterally extending flange 34 and a forwardly extending piece 36. Secured to the free end of the extending piece 36 is a valve end 38 formed with a port 40.

A sealing washer 4 is located immediately adjacent the lower (as shown) surface of the flange 34 and this washer 4 serves to seal the bottle adaptor 13 onto the top of the bottle neck (not shown) when the bottle neck threads are engaged with the internal threads 42 formed on a cap 2. The cap 2 as shown is mounted on the flange 34 and is freely rotatable around the main core 3.

Mounted around the cap 2 and substantially covering the cap is a freely rotatable outer sleeve 1. Formed in the wall of the outer sleeve 1 are slots 5 and 6 which match similar slots 8 and 9 in the cap 2. It will be evident that the slots 5 and 6 will engage with the lugs 13 on the coded collar 24 in the same way that the slots 8 and 9 in the cap 2 engage with lugs 13 on the coded collar 24. Thus, the lugs 13 on the coded collar 24 form the means by which torque is transmitted from the outer sleeve 1 to the cap 2 enabling said cap 2 to be rotated relative to the neck of the bottle 22 and to be secured to it.

A low friction washer 7 is located between the outer sleeve 1 and the cap 2 to facilitate rotation.

A washer 11 of an elastomeric material is located within the cap 2 in such a position that it is engaged by the neck of the bottle 22 onto which the cap 2 is positioned. The combination of the elastomeric washer 11 and the low friction washer 7 ensures that, when torque is applied to the outer sleeve 1 relative to a bottle on which the cap connector to is positioned, the outer sleeve 1 rotates relative to the cap 2, and the cap does not rotate relative to the neck of the bottle. This can facilitate the alignment of the slots 9 in the cap 2 with slots 5, 6 in the outer sleeve 1 and, if no collar lug 13 is present to engage with those slots 5 & 6, prevent the screwing of the cap 2 onto a bottle neck.

As shown in FIG. 3, the cap 2 projects slightly beyond the outer sleeve 1 to enable the user to engage the cap slots 8, 9 with the coded collar lugs 13 before rotating the sleeve 1 to similarly align the slots 5, 6 in outer sleeve 1 with the lugs 13 of the coded collar 24.

The slots 5, 6 in the outer sleeve 1 may be through slots but preferably are blind to provide more complete location around the profiles of the lugs 13 on the coded collar 24 and prevent the user locking the cap 2 and the outer sleeve 1 together with some foreign body.

It will be evident that if no coded collar 24 is arranged around the neck of the bottle then there is no drive possible between the outer sleeve 1 and the cap 2. Hence the bottle adaptor 16 cannot be connected to a bottle 22 without a coded collar 24.

Figure 5:
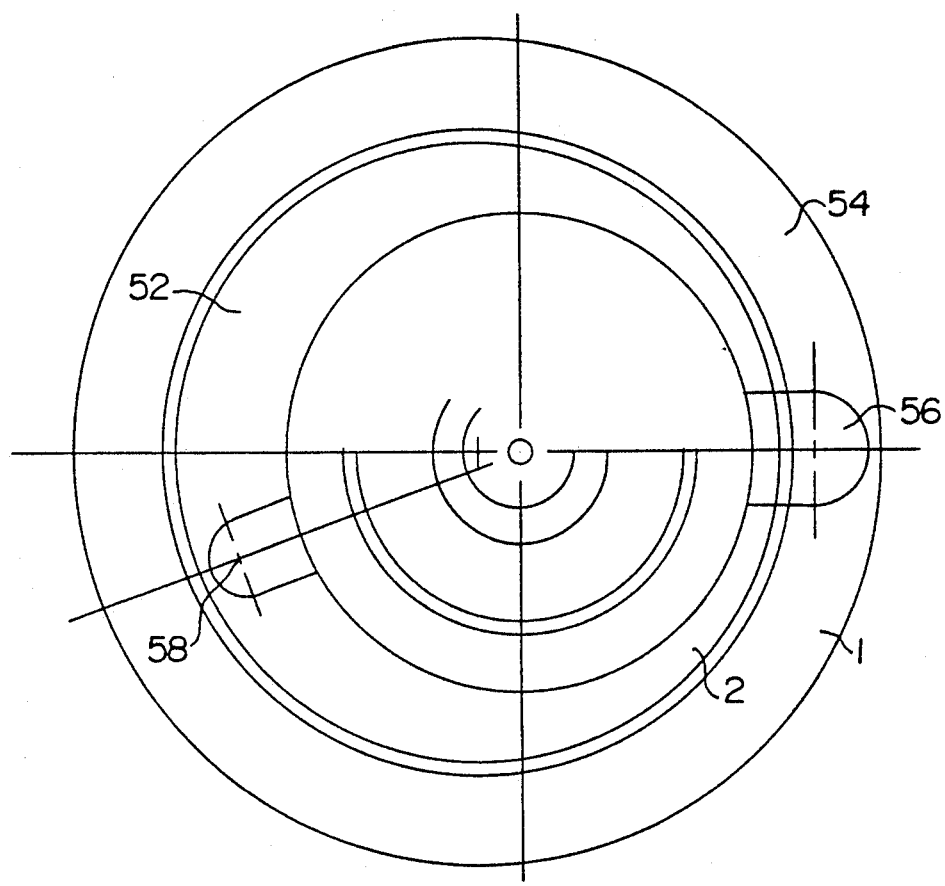
FIG. 5 is a plan view of another construction of cap connections.

FIG. 5 shows a construction of cap connector which comprises a cap 52 and an outer sleeve 54. A slot 56 is provided in the wall of the cap and the sleeve, and a further slot 58 is provided in the wall of the cap.

The wall thickness of the cap varies between minimum and maximum values at points which are diametrically opposite to one another, while the internal and external shapes of the cap are essentially circular, This arrangement can facilitate alignment of lugs on a collar provided on the neck of the bottle with the slots 56, 58. It will be noted that, in the construction shown in FIG. 5, the point at which the wall thickness of the cap is at a minimum is approximately coincident with the deeper of the two slots 56, 58.

We claim:

1. The combination of a bottle, collar and a cap connector for connecting the bottle to fluid delivery means, said collar being arranged and freely rotatable around the neck of the bottle and formed with at least one axially extending lug (13), the cap connector including a cap (2), said cap and the bottle having mating circumferentially extending screw threads, said cap including at least one axially extending slot for receiving said at least one axially extending lug of said collar, and an outer sleeve (1) freely rotatable least one axially extending slot in register with said at least one axially extending slot in said cap for receiving said at least one axially extending lug, the arrangement being such that mating of said axially extending lug with said at least one axially extending slot of said cap and said axially extending slot of said outer sleeve is necessary before relative rotation between said outer sleeve and said cap on the one hand, and the bottle on the other hand, is possible to screw said cap into engagement with the bottle.

2. A combination as claimed in claim 1 in which said cap connector includes a central main core (3) and said cap (2) and said outer sleeve (1) are freely rotatable about said central main core (3) of said cap connector.

3. A combination as claimed in claim 1, in which a low friction washer (7) is placed between a surface of the cap (2) and an adjacent surface of the outer sleeve (1).

4. A combination as claimed in claim 1 in which said cap (2) extends outwardly from said cap connector beyond said outer sleeve (1) towards the bottle.

5. A combination as claimed in claim 1 in which said at least one axially extending slot in said outer sleeve (1) is a blind slot.

6. A combination as claimed in claim 5, in which two or more axially extending lugs are provided on the collar.

* * * * *